US010781480B1

(12) United States Patent
Noor et al.

(10) Patent No.: US 10,781,480 B1
(45) Date of Patent: Sep. 22, 2020

(54) METHOD OF DETECTING NUCLEIC ACIDS WITH AMPLIFIED SIGNAL USING NANOPARTICLES (71) Applicant: ACGT Corporation, Toronto (CA)

(72) Inventors: Muhammad Omair Noor, Mississauga (CA); David Lawson Coburn, Toronto (CA); Hai Xing Chen, Toronto (CA)

(73) Assignee: ACGT Corporation, Toronto (CA)

(*) Notice: Subject to any disclaimer, the term of this patent is extended or adjusted under 35 U.S.C. 154(b) by 90 days.

(21) Appl. No.: 16/003,386

(22) Filed: Jun. 8, 2018

Related U.S. Application Data (60) Provisional application No. 62/528,078, filed on Jul. 1, 2017.

(51) Int. Cl.
*C12Q 1/68* (2018.01)
*C12Q 1/6848* (2018.01)

(52) U.S. Cl.
CPC .................. *C12Q 1/6848* (2013.01)

(58) Field of Classification Search
CPC .............. C12Q 1/682; C12Q 2563/149; C12Q 2565/519; C12Q 2537/143; C12Q 2525/161; G01N 33/54306; G01N 33/588
See application file for complete search history.

(56) References Cited

U.S. PATENT DOCUMENTS

| 6,261,779 B1 * | 7/2001 | Barbera-Guillem ........................ G01N 33/54306 435/6.11 |
| 2003/0165935 A1 * | 9/2003 | Vann ........................ B82Y 5/00 435/6.12 |
| 2006/0040286 A1 * | 2/2006 | Mirkin ................. C12Q 1/6816 435/6.11 |

* cited by examiner

*Primary Examiner* — Betty J Forman
(74) *Attorney, Agent, or Firm* — Cuspa Technology Law Associates; Yi Li (57) ABSTRACT

A method of detecting nucleic acids with an amplified signal utilizes first and second amplification nanoparticles. The method includes hybridizing a first segment and a second segment of a target sequence with a first capture probe on capture particles and a second capture probe on first amplification nanoparticles, respectively, and forming a capture particle-target-first amplification nanoparticle complex; adding second amplification nanoparticles and hybridizing the second linker probes on second amplification nanoparticles with first linker probes on the first amplification nanoparticles in the complex, wherein a ratio of the first linker probes to the second capture probes on first amplification particles is from about 1:1 to 50:1; hybridizing reporter probes with third linker probes on the second amplification nanoparticles, wherein a ratio of the third linker probes to the second linker probes on the second amplification particles is from about 3:1 to 20:1; and detecting signals from the reporter probes.

18 Claims, 3 Drawing Sheets

Specification includes a Sequence Listing.

METHOD OF DETECTING NUCLEIC ACIDS WITH AMPLIFIED SIGNAL USING NANOPARTICLES

CROSS REFERENCE TO RELATED APPLICATION

This application claims the benefit under 35 USC 119 (e) of the provisional patent application Ser. No. 62/528,078, filed Jul. 1, 2017, which is hereby incorporated by reference in its entirety.

FIELD OF THE INVENTION

The present invention relates to a method of detecting nucleic acids with amplified signals utilizing nanoparticles.

BACKGROUND OF THE INVENTION

In molecular diagnosis, the target DNA or RNA sequences in a sample are frequently at very low concentrations, which can be around or below the detection limit of available clinical diagnostic methods. This renders the analysis of these samples unreliable, or impossible.

The well-known PCR method was developed for solving this specific problem. In general, PCR based assays increase the concentration of a target sequence from its original concentration in the sample, and subsequently measure the target sequence after the PCR amplification. However, PCR based assays have complicated and lengthy sample preparation process, and require highly trained laboratory personals. The PCR based assays typically require up to 24 hours to obtain the analysis results.

It is desirable to be able to enhance the detectable signals of low concentration nucleic acids in a sample thereby improving detection sensitivity of an assay without relying on PCR amplification.

SUMMARY OF THE INVENTION

In some embodiments, the present invention is directed to a method of detecting nucleic acids with an amplified signal. In one embodiment, the method comprises exposing a single strand nucleic acid target sequence of interest to capture particles and first amplification nanoparticles, wherein each capture particle comprises one or more first capture probes immobilized thereon and each first capture probe comprises a first capture sequence complementary to a first segment of the target sequence, and wherein each first amplification nanoparticle comprises multiple second capture probes immobilized thereon and multiple first linker probes in a ratio to the second capture probes from about 1:1 to about 50:1, each second capture probe comprising a second capture sequence complementary to a second segment of the target sequence, and each first linker probe comprising a first linker sequence; and hybridizing the target sequence with the first and second capture sequences on the capture particles and first amplification nanoparticles, respectively, thereby forming a capture particle-target-first amplification nanoparticle complex; removing unbound first amplification nanoparticles; adding second amplification nanoparticles, wherein each second amplification nanoparticle has thereon multiple second linker probes and multiple third linker probes in a ratio to the second linker probe from about 1:1 to about 50:1, each second linker probe comprising a second linker sequence complementary to the first linker sequence of the first amplification nanoparticles, and each third linker probe comprising a third linker sequence; and hybridizing the second linker sequence on the second amplification nanoparticles with the first linker sequence of the first amplification nanoparticles thereby forming a capture particle-target-first amplification nanoparticle-second amplification nanoparticle complex; removing unbound second amplification nanoparticles; adding a reporter probe, each reporter probe comprising a reporter sequence complementary to the third linker sequence of the second amplification nanoparticles and a signal generating molecule, and hybridizing the reporter sequence with the third linker sequence of the second amplification nanoparticles; removing unbound reporter probe; detecting a signal from the signal generating molecule on the reporter probe; and determining the presence of the target sequence according to the signal.

In a further embodiment, the method comprises exposing a single strand nucleic acid target sequence of interest to capture particles and first amplification nanoparticles, wherein each capture particle comprises one or more first capture probes, each first capture probe comprising a first capture sequence with one terminus immobilized on the capture particle and a first click chemical functional group at another terminus of the first capture sequence, and the first capture sequence being complementary to a first segment of the target sequence, and wherein each first amplification nanoparticle comprises multiple second capture probes and multiple first linker probes in a ratio to the second capture probes from about 1:1 to about 50:1, each second capture probe comprising a second capture sequence with one terminus immobilized on the first amplification nanoparticle and a second click chemical functional group at another terminus of the second capture sequence chemically reactive to the first click chemical functional group and the second capture sequence being complementary to a second segment of the target sequence; and hybridizing the target sequence with the first and second capture sequences on the capture particles and the first amplification nanoparticles respectively, thereby forming a capture particle-target-first amplification nanoparticle complex in which the first and second click chemical functional groups form covalent bonds with each other; removing unbound first amplification nanoparticles; adding second amplification nanoparticles and a template sequence, wherein each second amplification nanoparticle has thereon multiple second linker probes and multiple third linker probes in a ratio to the second linker probe from about 1:1 to about 50:1, each third linker probe comprising a third linker sequence, wherein each first linker probe on the first amplification nanoparticle comprises a first linker sequence with one terminus immobilized on the first amplification nanoparticle and a third click chemical functional group at another terminus of the first linker sequence, the first linker sequence being complementary to a first segment of the template sequence, and wherein each second linker probe comprises a second linker sequence with one terminus immobilized on the second amplification nanoparticle and a fourth click chemical functional group at another terminus of the second linker sequence chemically reactive to the third click chemical functional group, the second linker sequence being complementary to a second segment of the template sequence; and hybridizing the template sequence with the first and second linker sequences on the first and second amplification nanoparticles respectively, thereby forming a capture particle-target-first amplification nanoparticle-template-second amplification nanoparticle complex, in which the third and fourth click chemical functional groups form covalent bonds with each other; removing unbound second amplification nanoparticles; adding a reporter probe, each reporter probe comprising a reporter sequence complementary to the third linker sequence of the second amplification nanoparticles and a signal generating molecule, and hybridizing the reporter sequence with the third linker sequence of the second amplification nanoparticles; removing unbound reporter probe; detecting a signal from the signal generating molecule on the reporter probe; and determining the presence of the target sequence according to the signal.

The advantages of the present invention will become apparent from the following description taken in conjunction with the accompanying drawings showing exemplary embodiments of the invention.

DETAILED DESCRIPTION OF THE INVENTION

Embodiments of the present invention generally relate to a method of detecting nucleic acids with amplified signals. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In some embodiments, the method utilizes nanoparticles to capture target nucleic acid sequence and amplify the signals correlating with the number of the target sequence to be detected. In one embodiment, the method comprises:

(a) exposing a single strand nucleic acid target sequence of interest to capture particles and first amplification nanoparticles, wherein each capture particle comprises one or more first capture probes immobilized thereon and each first capture probe comprises a first capture sequence complementary to a first segment of the target sequence, and wherein each first amplification nanoparticle comprises multiple second capture probes immobilized thereon and multiple first linker probes in a ratio to the second capture probes from about 1:1 to about 50:1, each second capture probe comprising a second capture sequence complementary to a second segment of the target sequence, and each first linker probe comprising a first linker sequence; and hybridizing the target sequence with the first and second capture sequences on the capture particles and first amplification nanoparticles respectively, thereby forming a capture particle-target-first amplification nanoparticle complex;

(b) removing unbound first amplification nanoparticles;

(c) adding second amplification nanoparticles, wherein each second amplification nanoparticle has thereon multiple second linker probes and multiple third linker probes in a ratio to the second linker probe from about 1:1 to about 50:1, each second linker probe comprising a second linker sequence complementary to the first linker sequence of the first amplification nanoparticles, and each third linker probe comprising a third linker sequence; and hybridizing the second linker sequence on the second amplification nanoparticles with the first linker sequence of the first amplification nanoparticles thereby forming a capture particle-target-first amplification nanoparticle-second amplification nanoparticle complex;

(d) removing unbound second amplification nanoparticles;

(e) adding a reporter probe, each reporter probe comprising a reporter sequence complementary to the third linker sequence of the second amplification nanoparticles and a signal generating molecule, and hybridizing the reporter sequence with the third linker sequence of the second amplification nanoparticles;

(f) removing unbound reporter probe;

(g) detecting a signal from the signal generating molecule on the reporter probe; and (h) determining the presence of the target sequence according to the signal.

Figure 1:
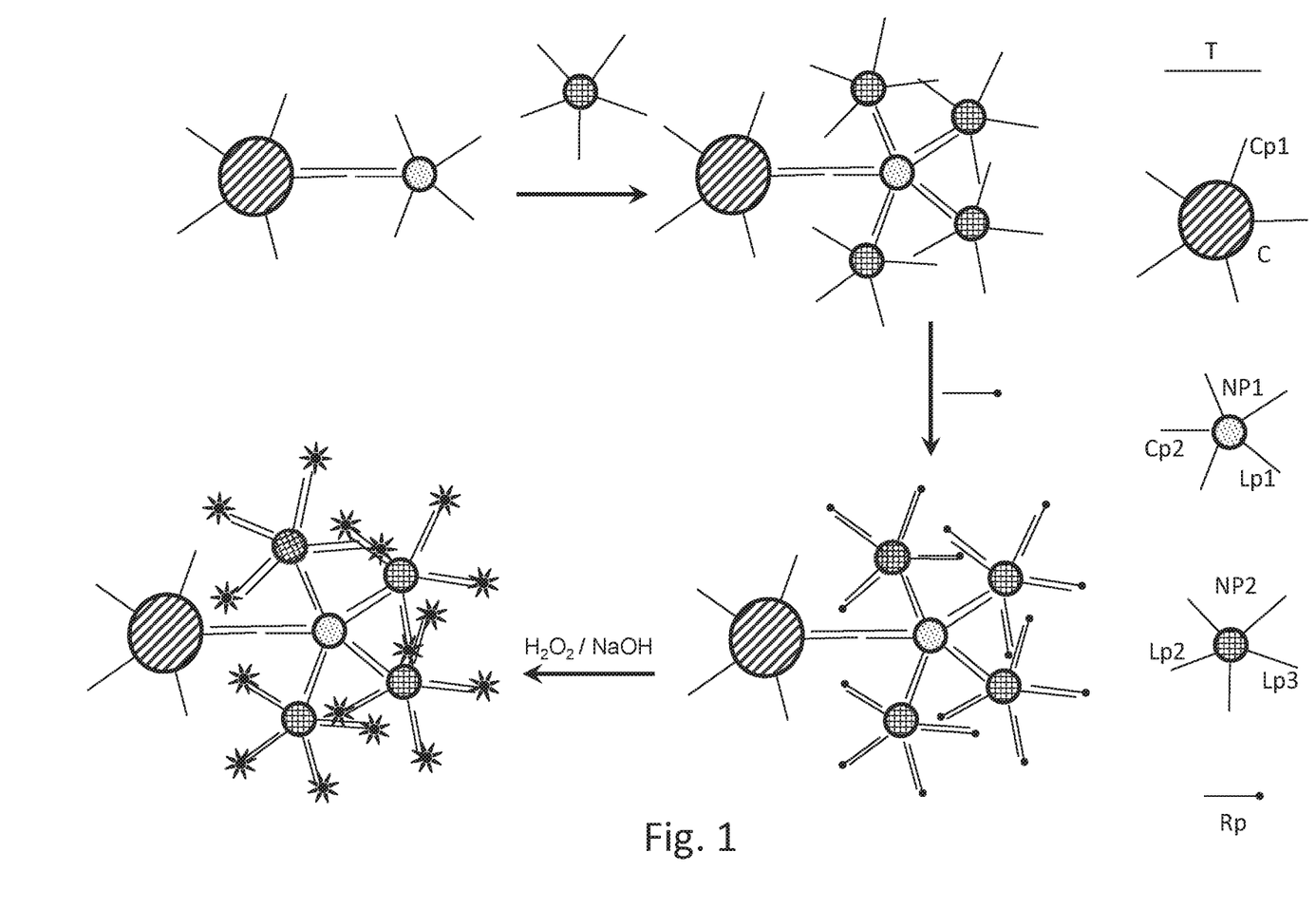
FIG. 1 illustrates schematically the method of the present invention in one embodiment. Individual components involved in the reactions are shown on the right.

The above process is illustrated schematically in FIG. 1. The structural features of the capture particles, first and second amplification nanoparticles, and reporter probe and the interactions of the above components in the process are described hereinafter.

The term "target sequence" used herein refers to a nucleic acid sequence to be detected, which can be a natural nucleic acid sequence in a biological sample, or a synthetic nucleic acid sequence. The target sequence has a first segment (Ts1) and a second segment (Ts2), each can hybridize with a complementary sequence on the capture particles and the first amplification nanoparticles, respectively, used in the present method.

In some embodiments, the capture particles may be magnetic particles, polystyrene particles or other polymer particles, with a diameter from about 0.5 to about 10 micrometers (μm). Each capture particle (C) includes one or more first capture probes (Cp1) immobilized thereon. The first capture probe comprises a single strand nucleic acid sequence complementary to the first segment of the target sequence of interest, which is herein referred to as the first capture sequence (Cs1). One terminus of the first capture sequence is immobilized on the capture particle and the other terminus is free from attachment which is herein referred to as free terminus. Various known methods of conjugation of oligonucleotides to metal or polymer particles can be used for preparing the capture particles for the present method. In some embodiments, the first capture sequence may further include a click chemical functional group at the free terminus as further described hereafter.

Commercially available magnetic particles or polystyrene particles can be used for the present method. For example, in one exemplary embodiment 2.8 micrometers (μm) magnetic particles from ThermoFischer Scientific (Ontario, Canada) were used. A first capture sequence complementary to a first segment of a particular target sequence can be synthesized using known methods and immobilized on the surface of the magnetic particles with known methods, such as using an affinity interaction between the streptavidin-coated magnetic particles and a biotin group on a terminus of the first capture sequence.

In some embodiments, the first amplification nanoparticles may be gold particles or polymer particles, with a diameter from about 5 to about 50 nanometers (nm). Each first amplification nanoparticle (NP1) comprises multiple second capture probes (Cp2) and multiple first linker probes (Lp1) immobilized thereon. The ratio of the first linker probes to the second capture probes on each first amplification nanoparticle may be from about 1:1 to about 50:1 and preferably from about 3:1 to about 20:1. Each second capture probe comprises a single strand nucleic acid sequence complementary to a second segment of the target sequence of interest, which is herein referred to as the second capture sequence (Cs2). Each first linker probe comprises a single strand nucleic acid sequence, which is herein referred to as the first linker sequence (Ls1). One terminus of the first linker sequence is immobilized on the first amplification nanoparticles. In some further embodiments, the first linker sequence may further include a click chemical functional group at its free terminus as further described hereinafter.

In some embodiments, the second amplification nanoparticle (NP2) comprises multiple second linker probes (Lp2) and multiple third linker probes (Lp3) immobilized thereon. In some embodiments, the ratio of the third linker probe to the second linker probe on each second amplification nanoparticle may be from about 1:1 to about 50:1 and preferably from about 3:1 to about 20:1. Each second linker probe comprises a single strand nucleic acid sequence complementary to the first linker sequence (Ls1) on the first amplification nanoparticles, which is herein referred to as the second linker sequence (Ls2). One terminus of the second linker sequence is immobilized on the second amplification nanoparticle. In some further embodiments, the free terminus of the second linker sequence may further include a click chemical functional group as further described hereafter. Each third linker probe (Lp3) comprises a single strand nucleic acid sequence with one terminus immobilized on the second amplification nanoparticle, which is herein referred to as the third linker sequence (Ls3).

In some embodiments, the second amplification nanoparticles may also be gold particles or polymer particles, with a diameter from about 5 to about 50 nanometers (nm). The size of the second amplification nanoparticles may be the same or different from the size of the first amplification nanoparticles. Commercially available gold nanoparticles can be used for the present method. For example, 5, 10, 15 and 30 nm gold nanoparticles from Cytodiagnostics (Ontario, Canada) may be used for preparing the first and second amplification nanoparticles described above.

A second capture sequence complementary to a second segment of a target sequence of interest and the linker sequences described above can be synthesized using known methods, and immobilized on the surface of the gold nanoparticles using known methods, such as using the gold-thiol interaction between the gold surface of the gold nanoparticles and a thiol functional group on a terminus of the second capture sequence or the linker sequence.

The reporter probe (Rp) comprises a single strand nucleic acid sequence complementary to the third linker sequence (Ls3) on the second amplification nanoparticles, which is herein referred to as a reporter sequence (Rs) and a signal generating molecule (S). In some embodiments, optionally the reporter probe may comprise a particle having the reporter sequence and multiple signal generating molecules immobilized thereon. After hybridization of the reporter sequence with the third linker sequence (Ls3) on the second amplification nanoparticles, the signals generated from the reporter probes are proportional to the number of reporter probes bound to the second amplification nanoparticles, which depends on various factors including the yield of formation of the capture particle-target-first amplification particle complex, the binding pattern and efficiency of the second amplification particles to the first amplification particles, as well as the ratio of the first linker probe to the second capture probe on the first amplification nanoparticles and the ratio of the third linker probe to the second linker probe on the second amplification nanoparticles as described further hereinafter.

Various known chemicals can be used as the signal generating molecule of the reporter probe. In some embodiments, the signal generating molecule is a chemiluminescent or fluorescent molecule, and the signal measurement can be carried out using chemiluminescence or fluorescence detectors. When the signal generating molecule is a chemiluminescent molecule, the method further comprises adding a chemiluminescent triggering solution prior to measuring the signal.

In an exemplary embodiment, acridinium $C_2$ NHS ester (4-(2-succinimidyl-oxycarbonylethyl) phenyl-10-acridinium-9-carboxylate trifluoromethyl sulfonate), from Cayman Chemicals (Ann Arbour, Mich.), was used as the signal generating molecule of the reporter probe. Acridinium $C_2$ NHS ester can be triggered by a hydrogen peroxide solution. Acridinium ester reacts instantaneously (about 1 to 5 seconds) with hydrogen peroxide under alkaline condition to produce a light signal at 430 nm. The signal can be measured by a luminometer.

Example first and second capture sequences have been synthesized, as shown in Table 1. It is noted that example capture probes, namely, Cp1 and Cp2, shown in Table 1 can be used either as the first capture probe or second capture probe as long as the probe is compatible with the particles used. Various linker sequences and reporter sequences have also been synthesized. The linker sequences are linear oligonucleotides which are not complimentary to the target sequence, nor to the first or second capture sequence, and do not hybridize with the target sequence, or the first or second capture sequence. The syntheses of the capture sequences, linker sequences and reporter sequences were completed using a standard protocol for linear oligonucleotide synthesis on an oligonucleotide synthesizer (ABI DNA Synthesizer, Forest City, Calif.). Furthermore, the oligonucleotide sequences with a functional group modification at either the 5' or 3' terminus or at both termini were purified by the reversed-phase high-pressure liquid chromatography.

further include a click chemical functional group. More specifically, in some embodiments the first capture probe of the capture particle further comprises a first click chemical functional group (F1) at the free terminus of the first capture sequence. On the other hand, the second capture probe of the first amplification nanoparticle further comprises a second click chemical functional group (F2) at the free terminus of the second capture sequence. The second click chemical functional group is chemically reactive to the first click

TABLE 1

Example Capture Sequences, Linker Sequences, and Reporter Sequences

| Probe/Sequence Name | Product Name | Sequence (5' to 3' direction) |
|---|---|---|
| First capture probe (Cp1) | DBCO TEG HBVF2 comp 6A bio | DBCO-TEG - 5'-GCA AAC CCC AAA AGA CCC ACA ATT AAA AAA-3'- Biotin (SEQ ID NO: 1) |
| First capture probe (Cp1) | HBVF2 comp 6A bio | 5'-GCA AAC CCC AAA AGA CCC ACA ATT AAA AAA-3'- Biotin (SEQ ID NO: 2) |
| Second capture probe (Cp2) | thiol S18 HBVR2 cap Azide | Thiol S18 - 5'- GCA GAT GAG AAG GCA CAG ACG-3'- Azide (SEQ ID NO: 3) |
| First linker probe (Lp1) | thiol S18 tgtv1 cap | Thiol S18 - 5'- GTC CGT TTC TCT TGG CTC AG-3' (SEQ ID NO: 4) |
| Second linker probe (Lp2) | thiol S18 tgtv1 comp | Thiol S18 - 5'-CTG AGC CAA GAG AAA CGG AC-3' (SEQ ID NO: 5) |
| Third linker probe (Lp3) | thiol S18 SMN1 cap | Thiol S18 - 5'-ATT TTG TCT GAA ACC CTG T-3' (SEQ ID NO: 6) |
| Reporter sequence (Rs) | amine SMN1 comp | Amine - 5'-ACA GGG TTT CAG ACA AAA T-3' (SEQ ID NO: 7) |
| Reporter sequence (Rs) | amine tgtv1 comp | Amine - 5'CTG AGC CAA GAG AAA CGG AC-3' (SEQ ID NO: 8) |
| Target sequence (T) | FC target (a) | 5'-AAT TGT GGG TCT TTT GGG GTT TGC CGT CTG TGC CTT CTC ATC TGC-3' (SEQ ID NO: 9) |
| Target sequence (T) | FC target (b) | 5'-AAT TGT GGG TCT TTT GGG GTT TGC GTC CGT TTC TCT TGG CTC AG-3' (SEQ ID NO: 10) |

Abbreviations:
FC = fully-complementary;
DBCO = dibenzocyclooctyne;
TEG = triethylene glycol;
bio = biotin;
S18 = spacer phosphoramidite 18. Further, the sequences "amine SMN1 comp" and "amine tgtv1 comp" were modified at the 5' end with acridinium ester (AE) (a chemiluminescence molecule) using acridinium NHS ester. The modified sequences are referred to as SMN1 comp AE and tgtv1 comp AE, respectively.
Note: In Table 1, the SEQ ID NO: 1 to SEQ ID NO: 8 refer to the respective nucleotide sequence without the chemical functional group(s) connected to the 5' end or the 3' end, or to both ends. The connection of a chemical function group to the respective sequence is expressed by a hyphen between the sequence and the chemical function group.

The sequence length of the linker sequences may be varied. In some embodiments, the linker sequences may have about 15 to 25 bases. Prior to synthesis of linker sequences, each linker sequence was put through NCBI (National Center for Biotechnology Information) BLASTN 2.2.6 to check if there were any significant matches in the database. This prevents potential non-specific binding of a linker probe to a nucleic acid region (viral, bacterial, human) other than their designated complementary sequences in the present method. The spacer in the capture sequence or linker sequence can be a number of non-specific nucleotides, a spacer phosphoramidite, or other suitable spacers known in the art.

Hybridization of the target sequence with the capture particles and the first amplification nanoparticles, and hybridization between the first and second amplification nanoparticles, and between the second amplification nanoparticles and the reporter probe can be carried out under known hybridization conditions. The hybridization can be carried out in a suitable reaction vessel, such as test tubes and containers.

As described above, the free terminus of the first capture sequence on the capture particles and the second capture sequence on the first amplification nanoparticle may each chemical functional group. Herein, the term of first and second click chemical functional groups refer to a pair of chemical functional groups that bind with each other covalently through a click chemistry reaction (or click reaction) when the two groups come in contact with each other. Known click chemistry reactions, such as Staudinger ligation, Huisgen 1,3-dipolar cycloaddition, their modifications and other click reactions, may be used in the present method. The Staudinger reaction is a chemical reaction of an azide with a phosphine or phosphite which produces an iminophosphorane. Huisgen 1,3-dipolar cycloaddition refers to a 1,3-dipolar cycloaddition between an organic azide and an alkyne to generate 1,2,3-triazole.

Figure 2:
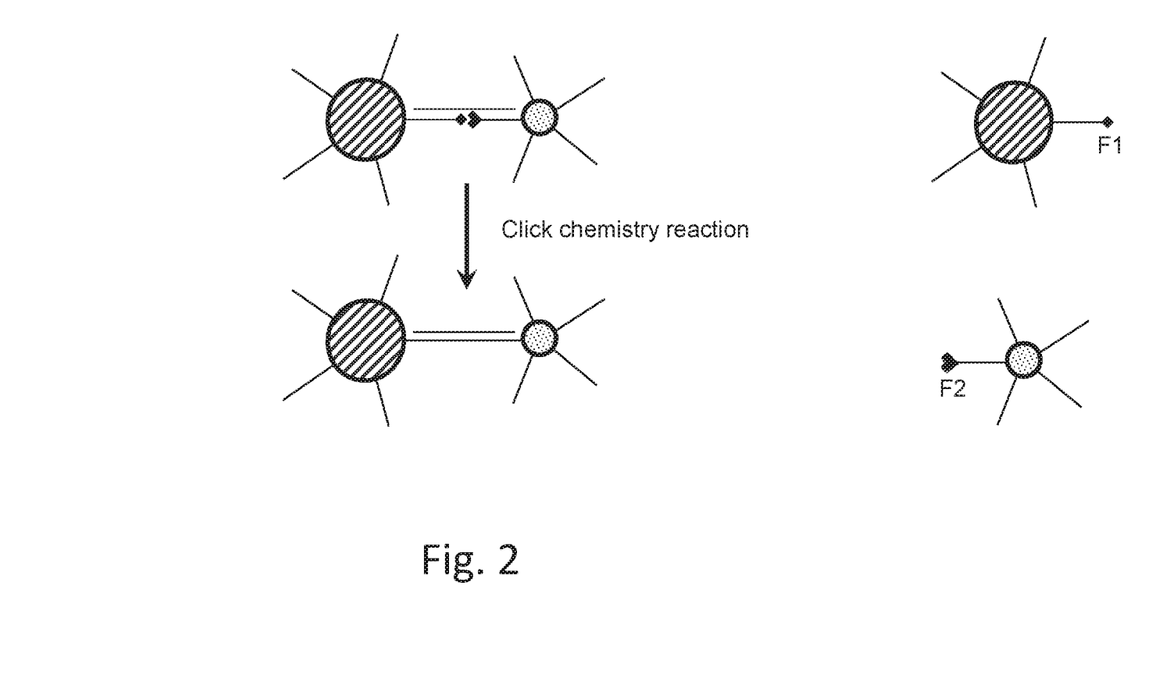
FIG. 2 illustrates schematically conjugation between two click chemical functional groups of the first and second capture sequences in the capture particle-target-first amplification nanoparticle complex initially formed by hybridization. Individual components involved in the reactions are shown on the right and in FIG. 1.

Click chemistry, more commonly called tagging, is a class of biocompatible reactions intended primarily to join substrates of choice with specific biomolecules, and it has been traditionally used for attaching a probe or substrate of interest to a specific biomolecule in a process of bioconjugation. In the present method, in step (a) of hybridizing the target sequence with the first and second capture sequences on the capture particles and first amplification nanoparticles respectively, the first click chemical functional group (F1) at the terminus of the first capture sequence comes in contact with the second click chemical functional group (F2) at the terminus of the second capture sequence, as shown in FIG. 2, and the two click chemical functional groups bind covalently with each other through a click chemistry reaction. In this embodiment, in the capture particle-target-first amplification nanoparticle complex (Complex-1A) formed, the first amplification nanoparticle is connected to the capture particle by both hydrogen bonds through hybridization of the target sequence and covalent bonds formed between the first and second capture probes. The covalent bonding between the two particles enhances the stability of the complex previously based on hydrogen bonding only, which benefits subsequent amplifications in the process.

Moreover, in an alternative embodiment the first linker probe of the first amplification nanoparticle may comprise a first linker sequence (Ls1a) and a third click chemical functional group (F3) at its free terminus, and the second linker probe of the second amplification nanoparticle may comprise a second linker sequence (Ls2a) and a fourth click chemical functional group (F4) at its free terminus. The fourth click chemical functional group is chemically reactive with the third click chemical functional group so that the two functional groups bind covalently with each other through a click chemistry reaction, similar to that described above in reference to the first and second click chemical functional groups. In this alternative embodiment, the first linker sequence (Ls1a) and the second linker sequence (Ls2a) are not complementary to each other. Instead, these two linker sequences are complementary to a first segment and a second segment, respectively, of a template sequence. Under a hybridization condition, the template sequence hybridizes with the first linker sequence (Ls1a) and the second linker sequence (Ls2a), and at the same time the third and fourth click chemical functional groups (F3, F4) conjugate with each other through a click chemistry reaction, in the same manner described above in reference to the first and second click chemical functional groups of the first and second capture probes. Therefore, the hybridization results in a capture particle-target-first amplification nanoparticle-template-second amplification nanoparticle complex (Complex-2A), in which the first and second amplification nanoparticles are connected by both hydrogen bonds between the template sequence and the first and second linker sequences and by covalent bonds between the third and fourth click chemical functional groups.

In this embodiment, the pair of third and fourth click chemical functional groups may be the same as or different from the pair of first and second click chemical functional groups. It is noted that the click chemistry reaction between a pair of click chemical functional groups is irreversible. Therefore, after removal of unbound first amplification nanoparticles, a further reaction between the third and fourth click chemical functional groups using the same click chemistry reaction between the first and second click chemical functional groups does not affect the conjugate formed between the capture particles and the first amplification nanoparticles.

In one exemplary embodiment, the first click chemical functional group on the first capture sequence is dibenzocyclooctyne (DBCO), and the second click chemical functional group on the second capture sequence is azide. This copper-free click chemistry reaction between dibenzocyclooctyne and azide forms a triazole linkage, which conjugates the two functional groups on the first and second capture probes respectively.

Each of the click functional groups described above can be connected to a terminus of respective sequence using appropriate click chemistry reagents, such as those commercially available click chemistry reagents. Various known chemical reactions for conjugation of a chemical functional group to an oligonucleotide can be used for connection of a click functional group to the terminus of respective sequence.

In a further embodiment, the first amplification nanoparticles may further include a plurality of supplementary reporter linker probes immobilized thereon, in addition to the second capture probes and the first linker probes. The supplementary reporter linker probes may be immobilized on the first amplification nanoparticles at various ratios of the second capture probes and the first linker probes. Each supplementary reporter linker probe comprises a reporter linker sequence which is a single strand nucleic acid sequence complementary to the reporter sequence (Rs) of the reporter probe, and can hybridize with the reporter sequence under a hybridization condition. With the first amplification nanoparticles in this embodiment in the process described above, when the reporter probes are added at the end of the detection process, the reporter probes not only hybridize with the third linker probes on the second amplification particles, but also hybridize with the supplementary reporter linker probes on the first amplification nanoparticles, which further increases the number of reporter probes that binds in the complex (Complex 2 or Complex 2A) and further amplifies the signal.

The process of detecting a subject nucleic acid using the present method is further described below in reference to FIG. 1. As schematically illustrated in FIG. 1, when a single strand nucleic acid target sequence (T) of interest is exposed to the capture particles (C) and the first amplification nanoparticles (NP1) under a hybridization condition, the target sequence hybridizes with the first and second capture sequences of the first and second capture probes (Cp1, Cp2) on the capture particles and the first amplification nanoparticles respectively, which forms the capture particle-target-first amplification nanoparticle complex (Complex-1) in which the first capture sequence anneals with the first segment of the target sequence and the second capture sequence anneals with the second segment of the target sequence.

In step (a) of the method described above, the target sequence may be exposed to the first amplification nanoparticles and the capture particles at the same time, or may be exposed to the two types of particles in a sequential manner. It has been found that the hybridization reaction between the target sequence and the second capture sequence on the conjugated gold nanoparticles proceeds rapidly and may take less than 5 minutes at room temperature. This may attribute to well suspended nanoparticles in the hybridization mixture, higher diffusion coefficient, and a high degree of freedom of the nanoparticles. Therefore, it may be advantageous to hybridize the target sequence first with the second capture sequence of the first amplification nanoparticles to form a partial complex, and then add the capture particles to hybridize the first capture sequence on the capture particles with the partial complex. This sequential process promotes fast hybridization of the target sequence using nanoparticles, and enhances overall efficiency of the process.

Unbound first amplification nanoparticles can be removed by proper means, for example, by subjecting the hybridization reaction mixture to a magnetic field to separate the complex (Complex-1) formed with capture particles made of magnetic particles. After washing, the second amplification nanoparticles are added under a hybridization condition. The second linker sequence of the second linker probe (Lp2) on the second amplification nanoparticles hybridizes with the first linker sequence of the first linker probe (Lp1) on the first amplification nanoparticles in the capture particle-target-first amplification nanoparticle complex (Complex-1), and forms a capture particle-target-first amplification nanoparticle-second amplification nanoparticle complex (Complex-2), as shown in FIG. 1.

After removing unbound second amplification nanoparticles, the reporter probes (Rp) are added and hybridized with the third linker sequence of the third linker probe (Lp3) on the second amplification nanoparticles (NP2). The unbound reporter probes can be removed by proper means, such as applying a magnetic field to the reaction mixture, or filtering the reaction mixture by a filter. After removing unbound reporter probes, signals (✱) generated by the signal generating molecule on the bounded reporter probes can then be detected. The presence of the target sequence, or quantitation of the target sequence in a sample can be determined according to the signal detected.

As further illustrated in FIG. 2, in the embodiments where the first capture probe on the capture particles further includes a first click chemical functional group (F1) at the free terminus of the first capture sequence and the second capture probe on the first amplification nanoparticle further includes a second click chemical functional group (F2) at the free terminus of the second capture sequence, the first and second click chemical functional groups (F1, F2) conjugate with each other during hybridization of the target sequence with the capture sequences on the two particles. In the formed capture particle-target-first amplification nanoparticle complex (Complex-1A), the first amplification nanoparticle is connected to the capture particle by both hydrogen bonds formed through hybridization with the target sequence and covalent bonds formed between the first and second capture probes, which enhances the stability of the complex.

It has been found that the present method enables amplification of signals by several orders of magnitude in comparison to traditional methods of capturing and detecting a target sequence using magnetic capture particles alone, and has significantly enhanced detection sensitivity. As can be appreciated, in the above method the amplification using conjugated gold nanoparticles involves two stages. The first stage involves binding of the target sequence with the first amplification nanoparticles and the capture particles, which is herein referred to as a primary amplification. The second stage involves binding of the second amplification nanoparticles to the first amplification nanoparticles in the capture particle-target-first amplification nanoparticle complex, which is herein referred to as a secondary amplification.

In the first stage, the signal amplification effects achieved using the gold nanoparticles conjugated with the second capture probes and the first linker probes may be related to the structure and properties of the conjugated gold nanoparticles in at least two aspects. Firstly, the conjugated gold nanoparticles substantially enhance the yield of formation of the complex between the target sequence and the capture probes. In comparison to a traditional method of capturing a target sequence using conjugated magnetic particles, using the instant conjugated gold nanoparticles to form a capture probe-target-first amplification nanoparticle complex, amplification of signals by two to three orders has been observed. This significant amplification may attribute to well suspended conjugated gold nanoparticles in the hybridization mixture, higher diffusion coefficient, improved accessible surface area for biomolecular reaction, and a high degree of freedom of the gold nanoparticles, which may have facilitated rapid binding of the target sequence to the conjugated gold nanoparticles in forming a partial complex and may have enhanced the efficiency of interaction between the partial complex with the capture particles. Further properties of the conjugated gold nanoparticles such as radius of curvature and higher density of immobilized oligonucleotides than planar surfaces may also render the first linker probes thereon more accessible for subsequent binding with other linker probes or reporter probes. Secondly, the ratio of the first linker probe to the second capture probe on each first amplification nanoparticle may be up to 50:1. As can be appreciated, in the embodiment where the ratio of the first linker probe to the second capture probe is from about 3:1 to about 20:1, in one capture particle-target-first amplification nanoparticle complex formed with one target sequence there are 3 to 20 first linker probes available, depending on the actual ratio of the first linker probe to the second capture probe used. This further increases available binding sites for subsequent binding with the second amplification nanoparticles.

In the second stage, the plurality of first linker probes on each first amplification nanoparticle (regardless of the ratio of the first linker probe to the second capture probe) in a capture particle-target-first amplification nanoparticle complex function as docking stations to anchor the second amplification nanoparticles. Therefore, a plurality of second amplification nanoparticles may bind to one first amplification nanoparticle, which substantially increases the number of the second amplification nanoparticles available for subsequent binding with the reporter probes. Moreover, similar to the second aspect discussed in the first stage, the ratio of the third linker probe to the second linker probe on each second amplification nanoparticle may be up to 50:1. As such, in the embodiment where the ratio of the third linker probe to the second linker probe is from about 3:1 to about 20:1, in the capture particle-target-first amplification nanoparticle-second amplification nanoparticle complex, for each bound second linker probe, there are 3 to 20 third linker probes available, depending on the actual ratio of the third linker probe to the second linker probe used, for the subsequent binding with the reporter probes. This further increases available binding sites for the reporter probes.

The effect of the primary amplification is assessed in Example 3. In the example, the FC target (a) and tgtv1 comp AE shown in Table 1 were used as the target sequence and reporter probe, respectively, and DBCO TEG HBVF2 comp 6A bio oligonucleotide conjugated magnetic beads obtained from Example 1 were used as the capture particles. The thiol S18 HBVR2 cap Azide and thiol S18 tgtv1 cap oligonucleotides conjugated gold nanoparticles obtained from Example 2 were used as the first amplification particles, in which the ratio of the second capture probe (thiol S18 HBVR2 cap Azide) to the first linker probe (thiol S18 tgtv1 cap) was 1:9 according to the process described in Example 2. In this example, the hybridization reactions with and without a click chemistry reaction between the first and second capture probes were tested. After the hybridization reaction to form the capture particle-target-first amplification nanoparticle complex (either Complex-1 or Complex-1A), a reporter probe complementary to the first linker sequence is added.

Figure 3:
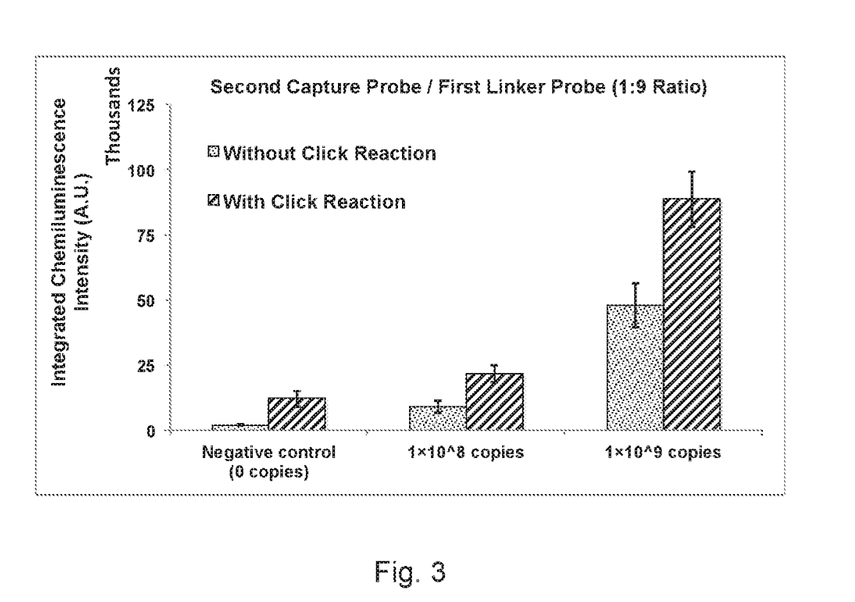
FIG. 3 shows the results of measurements of a target sequence using the present method as described in Example 3.

FIG. 3 shows the intensity of chemiluminescence signals detected at different concentrations of the target sequence illustrated in bar graphs. As shown, with or without a click chemistry reaction between the first and second capture probes on the capture particles and the first amplification nanoparticles respectively, using the primary amplification of the present method, the target sequence at a concentration of $1\times10^8$ copies and $1\times10^9$ copies can be detected. The signal amplitude correlates with the target sequence concentration tested. As further seen in FIG. 3, substantially further signal enhancement has been observed with the capture particle-target-first amplification nanoparticle complex (Complex-1A) in which the first and second capture probes are conjugated by the two click functional groups.

Figure 4:
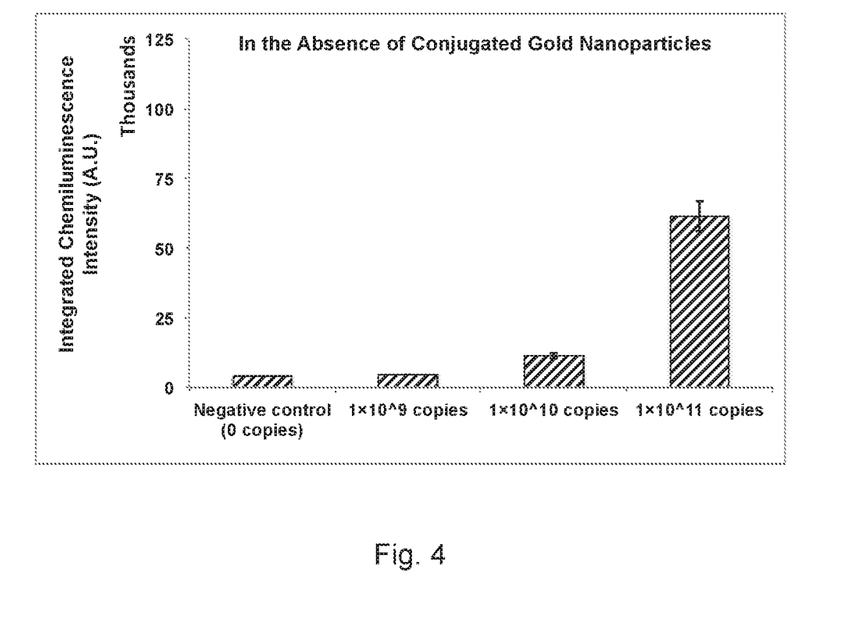
FIG. 4 is shows the results of measurements of a target sequence using a traditional method as described in Example 5.

In contrast, as shown FIG. 4, using a traditional method as a comparison test as described in Example 5, the target sequence can only be detected at a minimum concentration of $1\times10^{10}$ copies.

Therefore, the primary amplification of the method significantly improves detection sensitivity in measuring nucleic acids in comparison to the traditional method. The second amplification of the method further substantially increases the binding sites for the reporter probes as described above and further enhances the detection sensitivity. The present method can be used as a sensitive and low cost method in measurement of the nucleic acids.

Following examples further illustrate preparations of the capture particles and linker nanoparticles and the process of detecting target nucleic acid using the present method.

Example 1: Preparation of Capture Particles

Streptavidin magnetic beads (SAvMBs) of average diameter 2.8 μm under a product name of Dynabeads® M-270 from ThermoFischer Scientific (Ontario, Canada) were used for preparing the capture particles. DBCO TEG HBVF2 comp 6A bio or HBVF2 comp 6A bio oligonucleotide shown in Table 1 was used for the first capture probe. DBCO TEG HBVF2 comp 6A bio oligonucleotide included a click functional group (DBCO) at the 5' terminus, and no click functional group was attached to HBVF2 comp 6A bio oligonucleotide. The oligonucleotide was conjugated to the streptavidin magnetic beads by the following process.

A 100 μL aliquot of stock SAvMBs was washed 5 times with 200 μL of a phosphate buffered saline containing 0.01% Tween® 20 (polysorbate 20) (PBS1) using a magnetic capture stand. The streptavidin magnetic beads were then resuspended in 100 μL of a phosphate buffered saline containing 0.01% Tween® 20 and 1 M NaCl (PBS2). To the streptavidin magnetic beads, 0.4 nmol of either DBCO TEG HBVF2 comp 6A bio or HBVF2 comp 6A bio oligonucleotide shown in Table 1 was added and mixed overnight on a vortex mixer. Bioconjugation between the streptavidin magnetic beads and either DBCO TEG HBVF2 comp 6A bio or HBVF2 comp 6A bio oligonucleotide formed the capture particles. The conjugated magnetic beads were then washed 5 times with 200 μL of PBS1 and subsequently resuspended in 200 μL of PBS2 (2× diluted).

Example 2: Preparation of Amplification Nanoparticles

Colloidal non-functionalized standard gold nanoparticles (AuNPs) of average diameter 15 nm from Cytodiagnostics (Ontario, Canada) were used to prepare amplification nanoparticles. The thiol S18 HBVR2 cap Azide and thiol S18 tgtv1 cap oligonucleotides shown in Table 1 were used for the second capture probe and the first linker probe, respectively, of an example first amplification nanoparticles. The thiol S18 HBVR2 cap Azide oligonucleotide included a click functional group (Azide) at the 3' terminus, and no click functional group was attached to thiol S18 tgtv1 cap oligonucleotide. The two oligonucleotides were conjugated to the 15 nm gold nanoparticles by the following process.

Citrate-capped 15 nm AuNPs were concentrated to 30 nM concentration using centrifugation. Each of the thiol S18 HBVR2 cap Azide and thiol S18 tgtv1 cap oligonucleotides was added at 250 times the molar excess of the AuNPs concentration in the presence of 0.1% Tween® 20 and mixed for 30 minutes. The solution concentration of NaCl was then increased to 1 M in 0.1 M increments, where each incremental addition of NaCl was followed by a sonication step for about 10 seconds and then agitated for 20 minutes. The reaction mixture was then agitated overnight on an orbital shaker. Following overnight reaction, poly(ethylene glycol) methyl ether thiol with average molecular weight of 800 Daltons (mPEGthiol 800) from Sigma-Aldrich (Ontario, Canada) was added to the reaction mixture at 10 times the molar excess of the oligonucleotides concentration and agitated for additional 1 hour.

The conjugated gold nanoparticles were then purified by centrifugation to leave a pellet of conjugated gold nanoparticles at the bottom of the tube while the supernatant was discarded. The pellet was then resuspended in PBS1 and the centrifugation step was repeated. This procedure was repeated for additional three times and the conjugated gold nanoparticles were finally dispersed in 50 mM borate buffered saline containing 100 mM NaCl and 0.01% Tween® 20 (BBS1). The concentration of the conjugated gold nanoparticles was then determined by absorbance spectroscopy.

To obtain different ratios between the second capture probe and the first linker probe on the conjugated gold nanoparticles, the thiol S18 HBVR2 cap Azide and thiol S18 tgtv1 cap oligonucleotides at different ratios were added accordingly in the process described in this example.

Similarly, the second amplification particles are prepared with the above bioconjugation process using the same gold nanoparticles and thiol S18 tgtv1 comp and thiol S18 SMN1 cap oligonucleotides shown in Table 1 for the second and third linker probes. Moreover, the thiol S18 tgtv1 comp and thiol S18 SMN1 cap oligonucleotides at different ratios are added to obtain the second amplification particles with different ratios of the second and third linker probes.

Example 3: Detection of Target Sequence with First Amplification

The FC target (a) and tgtv1 comp AE shown in Table 1 were used as the target sequence and the reporter probe, respectively. DBCO TEG HBVF2 comp 6A bio or HBVF2 comp 6A bio oligonucleotide conjugated magnetic beads obtained from Example 1 were used as the capture particles. The thiol S18 HBVR2 cap Azide and thiol S18 tgtv1 cap conjugated gold nanoparticles obtained from Example 2 were used as the first amplification particles, which had thereon a 1:9 ratio of the second capture probe to the first linker probe (i.e., the ratio of thiol S18 HBVR2 cap Azide to thiol S18 tgtv1 cap oligonucleotides).

Moreover, in the hybridization reaction with a click chemistry reaction, DBCO TEG HBVF2 comp 6A bio oligonucleotide conjugated magnetic beads were used as the capture particles, where the terminal DBCO group on the magnetic beads reacts with the Azide functional group on the second capture probe (thiol S18 HBVR2 cap Azide) in the thiol S18 HBVR2 cap Azide and thiol S18 tgtv1 cap oligonucleotide conjugated gold nanoparticles. In the hybridization reaction without the click chemistry reaction, HBVF2 comp 6A bio oligonucleotide conjugated magnetic beads were used as the capture particles, which does not carry a click functional group (namely lacking the DBCO group) to react with the Azide functional group on the second capture probe in the thiol S18 HBVR2 cap Azide and thiol S18 tgtv1 cap oligonucleotide conjugated gold nanoparticles, and therefore, does not enable a click chemistry reaction. The detection process was the same with or without a click chemistry reaction as described below.

Serial dilutions of the FC target (a) ranging in concentration from 8.88 pM to 0.888 µM were prepared using a 50 mM borate buffered saline (pH 9.2) containing 1 M NaCl and 0.01% Tween® 20 (BBS2). 2 µL of 2× diluted DBCO TEG HBVF2 comp 6A bio or HBVF2 comp 6A bio conjugated magnetic beads were added to 18.7 µL of the FC target (a) solution at various concentrations in the presence of 6 µL of 1.81 nM 15 nm thiol S18 HBVR2 cap Azide and thiol S18 tgtv1 cap oligonucleotide conjugated gold nanoparticles. The hybridization reaction was allowed to proceed for 1 to 3 hours to form a conjugated magnetic bead-FC target-conjugated gold nanoparticle complex. The complex formed were then captured using a magnetic stand, washed three times with BBS1 and resuspended in 100 µL of PBS2. Then, 16 µM tgtv1 comp AE was added and hybridized to the complex. The final reaction product is then washed with PBS2 using a magnetic capture stand to remove unbound tgtv1 comp AE and then used to measure chemiluminescence signals.

The detection results, namely, the intensity of chemiluminescence signals at different FC target (a) concentrations are shown in FIG. 3. As shown, with or without a click chemistry reaction between the first and second capture probes, the target sequence at a concentration of $1 \times 10^8$ copies and $1 \times 10^9$ copies was detected, and the signal amplitude correlated with the concentrations of the target sequences tested. Moreover, substantially further signal enhancement was observed with the pair of particles which enable the click chemistry reaction between the first and second capture probes upon target hybridization and conjugate the first and second capture probes in the complex formed.

Example 4: Detection of Target Sequence with Two Step Amplifications

The FC target (a) shown in Table 1 is used as the target sequence and DBCO TEG HBVF2 comp 6A bio or HBVF2 comp 6A bio oligonucleotide conjugated magnetic beads obtained from Example 1 are used as the capture particles. The gold nanoparticles conjugated with thiol S18 HBVR2 cap Azide and thiol S18 tgtv1 cap as obtained from Example 2 are used as the first amplification particles. The gold nanoparticles conjugated with thiol S18 tgtv1 comp and thiol S18 SMN1 cap oligonucleotides shown in Table 1 prepared with the process of Example 2 are used as the second amplification particles. The SMN1 comp AE shown in Table 1 is used as the reporter probe.

The same process described in Example 3 is used to form a conjugated magnetic bead-FC target-first conjugated gold nanoparticle complex. Then, gold nanoparticles conjugated with thiol S18 tgtv1 comp and thiol S18 SMN1 cap oligonucleotides are added. The hybridization reaction is allowed to proceed for 1 to 3 hours to form a conjugated magnetic bead-FC target-first conjugated gold nanoparticle-second conjugated gold nanoparticle complex. The complex formed are then captured using a magnetic stand, washed three times with BBS1 and resuspended in 100 µL of PBS2.

Then, 16 µM SMN1 comp AE is added and hybridized to the complex. The final reaction product is then washed with PBS2 using a magnetic capture stand to remove unbound SMN1 comp AE and then used to measure chemiluminescence signals.

Example 5: Detection of Target Sequence Using Traditional Method

For the purpose of comparison, a detection of a target sequence using capture particles alone in the absence of the conjugated gold nanoparticles (the first amplification particles) was carried out. Here, the HBVF2 comp 6A bio oligonucleotide conjugated magnetic beads obtained from Example 1 were used as the capture particles, and the FC target (b) and tgtv1 comp AE shown in Table 1 were used as the target sequence and the reporter probe, respectively. In this case, the HBVF2 comp 6A bio oligonucleotide sequence is complementary to one segment of FC target (b) and tgtv1 comp AE is complementary to the other segment of FC target (b).

The same target sequence concentrations and test procedure described above in Example 3 were used, except that no conjugated gold nanoparticles were added. The hybridization reaction forms a conjugated magnetic bead-FC target complex in which one segment of the target sequence remains as a single strand nucleic acid. After addition of tgtv1 comp AE as described above in Example 3, the reporter probe hybridizes with the single strand nucleic acid in the complex. After washing as described above in Example 3, the chemiluminescence signals were measured. The result is shown in FIG. 4.

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of detecting nucleic acids with an amplified signal, comprising:

exposing a single strand nucleic acid target sequence of interest to capture particles and first amplification nanoparticles, wherein each capture particle comprises one or more first capture probes immobilized thereon and each first capture probe comprises a first capture sequence complementary to a first segment of the target sequence, and wherein each first amplification nanoparticle comprises multiple second capture probes immobilized thereon and multiple first linker probes in a ratio to the second capture probes from about 1:1 to about 50:1, each second capture probe comprising a second capture sequence complementary to a second segment of the target sequence, and each first linker probe comprising a first linker sequence; and hybridizing the target sequence with the first and second capture sequences on the capture particles and first amplification nanoparticles, respectively, thereby forming a capture particle-target-first amplification nanoparticle complex;

removing unbound first amplification nanoparticles;

adding second amplification nanoparticles, wherein each second amplification nanoparticle has thereon multiple second linker probes and multiple third linker probes in a ratio to the second linker probe from about 1:1 to about 50:1, each second linker probe comprising a second linker sequence complementary to the first linker sequence of the first amplification nanoparticles, and each third linker probe comprising a third linker sequence different from the second linker sequence and with a binding specificity to a reporter probe; and hybridizing the second linker sequence on the second amplification nanoparticles with the first linker sequence of the first amplification nanoparticles thereby forming a capture particle-target-first amplification nanoparticle-second amplification nanoparticle complex;

removing unbound second amplification nanoparticles;

adding said reporter probe, each reporter probe comprising a reporter sequence complementary to the third linker sequence of the second amplification nanoparticles and a signal generating molecule, and hybridizing the reporter sequence with the third linker sequence of the second amplification nanoparticles; thereby forming a final complex in which the reporter probe is bound specifically with the third linker sequence of the second amplification nanoparticles, without binding with the second linker sequence of the second amplification nanoparticles;

removing unbound reporter probe;

detecting a signal from the signal generating molecule on the reporter probe; and determining the presence of the target sequence according to the signal.

2. The method of claim 1, the ratio of the first linker probes to the second capture probes on the first amplification particles is from about 3:1 to about 20:1.

3. The method of claim 1, wherein the ratio of the third linker probes to the second linker probes on the second amplification particles is from about 3:1 to about 20:1.

4. The method of claim 1, the first and second amplification nanoparticles are gold or polymer nanoparticles.

5. The method of claim 1, wherein the first and second amplification nanoparticles are from about 5 to about 50 nanometers (nm).

6. The method of claim 1, wherein the capture particles are magnetic particles or polymer particles.

7. The method of claim 1, wherein the capture particles are from about 0.5 to about 10 micrometers (μm).

8. The method of claim 1, wherein the first capture probe of the capture particle has one terminus of the first capture sequence immobilized on the capture particle and further comprises a first click chemical functional group at another terminus of the first capture sequence, and the second capture probe of the first amplification nanoparticle has one terminus of the second capture sequence immobilized on the first amplification nanoparticle and further comprises a second click chemical functional group at another terminus of the second capture sequence chemically reactive to the first click chemical functional group, and wherein when hybridizing the target sequence with the first and second capture sequences on the capture particle and the first amplification nanoparticle respectively, the first and second click chemical functional groups are brought into proximity to form covalent bonds with each other in the capture particle-target-first amplification nanoparticle complex.

9. The method of claim 1, wherein the signal generating molecule of the reporter probe is a chemiluminescence or a fluorescence molecule.

10. The method of claim 1, wherein the first amplification particle further comprises multiple supplementary reporter linker probes immobilized thereon, and each supplementary reporter linker probe comprises a reporter linker sequence complementary to the reporter sequence of the reporter probe.

11. A method of detecting nucleic acids with an amplified signal, comprising:

exposing a single strand nucleic acid target sequence of interest to capture particles and first amplification nanoparticles, wherein each capture particle comprises one or more first capture probes, each first capture probe comprising a first capture sequence with one terminus immobilized on the capture particle and a first click chemical functional group at another terminus of the first capture sequence, and the first capture sequence being complementary to a first segment of the target sequence, and wherein each first amplification nanoparticle comprises multiple second capture probes and multiple first linker probes in a ratio to the second capture probes from about 1:1 to about 50:1, each second capture probe comprising a second capture sequence with one terminus immobilized on the first amplification nanoparticle and a second click chemical functional group at another terminus of the second capture sequence chemically reactive to the first click chemical functional group and the second capture sequence being complementary to a second segment of the target sequence; and hybridizing the target sequence with the first and second capture sequences on the capture particles and the first amplification nanoparticles respectively, thereby forming a capture particle-target-first amplification nanoparticle complex in which the first and second click chemical functional groups form covalent bonds with each other;

removing unbound first amplification nanoparticles;

adding second amplification nanoparticles and a template sequence, wherein each second amplification nanoparticle has thereon multiple second linker probes and multiple third linker probes in a ratio to the second linker probe from about 1:1 to about 50:1, each third linker probe comprising a third linker sequence, wherein each first linker probe on the first amplification nanoparticle comprises a first linker sequence with one terminus immobilized on the first amplification nanoparticle and a third click chemical functional group at another terminus of the first linker sequence, the first linker sequence being complementary to a first segment of the template sequence, and wherein each second linker probe comprises a second linker sequence with one terminus immobilized on the second amplification nanoparticle and a fourth click chemical functional group at another terminus of the second linker sequence chemically reactive to the third click chemical functional group, the second linker sequence being complementary to a second segment of the template sequence; and hybridizing the template sequence with the first and second linker sequences on the first and second amplification nanoparticles respectively, thereby forming a capture particle-target-first amplification nanoparticle-template-second amplification nanoparticle complex, in which the third and fourth click chemical functional groups form covalent bonds with each other;

removing unbound second amplification nanoparticles;

adding a reporter probe, each reporter probe comprising a reporter sequence complementary to the third linker sequence of the second amplification nanoparticles and a signal generating molecule, and hybridizing the reporter sequence with the third linker sequence of the second amplification nanoparticles;

removing unbound reporter probe;

detecting a signal from the signal generating molecule on the reporter probe; and determining the presence of the target sequence according to the signal.

12. The method of claim 11, the ratio of the first linker probes to the second capture probes on the first amplification particles is from about 3:1 to about 20:1.

13. The method of claim 11, wherein the ratio of the third linker probes to the second linker probes on the second amplification particles is from about 3:1 to about 20:1.

14. The method of claim 11, wherein the first and second amplification nanoparticles are gold nanoparticles.

15. The method of claim 11, wherein the first and second amplification nanoparticles are from about 5 to about 50 nanometers (nm).

16. The method of claim 11, wherein the capture particles are magnetic particles.

17. The method of claim 11, wherein the capture particles are from about 0.5 to about 10 micrometers (μm).

18. The method of claim 11, wherein the first amplification particle further comprises multiple supplementary reporter linker probes immobilized thereon, and each supplementary reporter linker probe comprises a reporter linker sequence complementary to the reporter sequence of the reporter probe.

* * * * *

SEQUENCE LISTING

```
<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
```

-continued

```
<223> OTHER INFORMATION: Probe

<400> SEQUENCE: 1
gcaaacccca aaagacccac aattaaaaaa                                    30

<210> SEQ ID NO 2
<211> LENGTH: 30
<212> TYPE: DNA
<213> ORGANISM: Artificial Sequence
<220> FEATURE:
<223> OTHER INFORMATION: Probe

<400> SEQUENCE: 2
gcaaacccca aaagacccac aattaaaaaa                                    30

<210> SEQ ID NO 3
<211> LENGTH: 21
<212> TYPE: DNA
<213> ORGANISM: Artificial Sequence
<220> FEATURE:
<223> OTHER INFORMATION: Probe

<400> SEQUENCE: 3
gcagatgaga aggcacagac g                                             21

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
gtccgtttct cttggctcag                                               20

<210> SEQ ID NO 5
<211> LENGTH: 20
<212> TYPE: DNA
<213> ORGANISM: Artificial Sequence
<220> FEATURE:
<223> OTHER INFORMATION: Probe

<400> SEQUENCE: 5
ctgagccaag agaaacggac                                               20

<210> SEQ ID NO 6
<211> LENGTH: 19
<212> TYPE: DNA
<213> ORGANISM: Artificial Sequence
<220> FEATURE:
<223> OTHER INFORMATION: Probe

<400> SEQUENCE: 6
attttgtctg aaaccctgt                                                19

<210> SEQ ID NO 7
<211> LENGTH: 19
<212> TYPE: DNA
<213> ORGANISM: Artificial Sequence
<220> FEATURE:
<223> OTHER INFORMATION: Probe

<400> SEQUENCE: 7
acagggtttc agacaaaat                                                19
```

```
<210> SEQ ID NO 8
<211> LENGTH: 20
<212> TYPE: DNA
<213> ORGANISM: Artificial Sequence
<220> FEATURE:
<223> OTHER INFORMATION: Probe

<400> SEQUENCE: 8
ctgagccaag agaaacggac                                                    20

<210> SEQ ID NO 9
<211> LENGTH: 45
<212> TYPE: DNA
<213> ORGANISM: Artificial Sequence
<220> FEATURE:
<223> OTHER INFORMATION: Probe

<400> SEQUENCE: 9
aattgtgggt cttttggggt ttgccgtctg tgccttctca tctgc                        45

<210> SEQ ID NO 10
<211> LENGTH: 44
<212> TYPE: DNA
<213> ORGANISM: Artificial Sequence
<220> FEATURE:
<223> OTHER INFORMATION: Probe

<400> SEQUENCE: 10
aattgtgggt cttttggggt ttgcgtccgt ttctcttggc tcag                         44
```